United States Patent [19]

Soula et al.

[11] 4,408,075

[45] Oct. 4, 1983

[54] PROCESS FOR THE PREPARATION OF TRIS-(ETHER-AMINES) AND THE TRIS-(ETHER-AMINES) PRODUCED

[75] Inventors: Gerard Soula, Meyzieu; Louis Linguenheld, Saint-Genis-Laval, both of France

[73] Assignee: Rhone-Poulenc Industries, Paris, France

[21] Appl. No.: 142,258

[22] Filed: Apr. 21, 1980

[30] Foreign Application Priority Data

May 3, 1979 [FR] France ................................. 79 11100

[51] Int. Cl.³ ............................................. C07C 91/02
[52] U.S. Cl. ................................. 564/474; 564/347; 564/480; 564/505
[58] Field of Search ................ 564/474, 480, 505, 347

[56] References Cited

U.S. PATENT DOCUMENTS

| | | | |
|---|---|---|---|
| 2,285,419 | 6/1942 | Dickey et al. | 564/480 |
| 2,323,658 | 7/1943 | Hester | 564/505 X |
| 2,325,514 | 7/1943 | Hester | 564/505 X |
| 2,355,337 | 8/1944 | Spence | 564/505 X |
| 2,365,721 | 12/1944 | Olin et al. | 564/480 |
| 2,928,877 | 3/1960 | Marion et al. | 564/505 |
| 3,278,598 | 10/1966 | Markiewitz | 564/480 X |
| 3,347,926 | 10/1967 | Zeck | 564/480 |
| 4,014,933 | 3/1977 | Boettger et al. | 564/480 X |

FOREIGN PATENT DOCUMENTS

| | | | |
|---|---|---|---|
| 849348 | 6/1977 | Belgium | 564/480 |
| 1302365 | 7/1962 | France | 564/480 |

*Primary Examiner*—Robert V. Hines

[57] ABSTRACT

A process of preparing tris-(ether-amines) of the formula:

$$N-[A-O-(B-O)_n-R]_3$$

in which R represents a hydrocarbon radical, A and B represent alkanediyl radicals, and n is a whole number between zero and 4, by ammonolysis of an alkylene glycol mono-ether of the formula:

$$HO-A-O-(B-O)_n-R$$

in the presence of 10 to 40 percent by weight of a hydrogenation-dehydrogenation catalyst, based on weight of said alkylene glycol monoether.

The tris-(ether-amines) produced, such as tris-(3,6-dioxa-octyl)amine, tris-(3,6,9-trioxaundecyl)amine, tris-(3,6-dioxaheptyl)amine, and tris-(3,6-dioxadecyl)amine.

19 Claims, No Drawings

PROCESS FOR THE PREPARATION OF TRIS-(ETHER-AMINES) AND THE TRIS-(ETHER-AMINES) PRODUCED

BACKGROUND OF THE INVENTION

The present invention relates to a process for the preparation of tris-(ether-amines) of formula (I):

$$N\text{-}[A\text{-}O\text{-}(B\text{-}O)_n R]_3 \qquad (I)$$

in which R represents a member selected from an alkyl radical containing from about 1 to 24 carbon atoms, a cyclohexyl radical, a phenyl radical, and an alkylphenyl radical whose alkyl group contains from about 1 to 12 carbon atoms;

A and B are similar or different and represent a linear alkanediyl group containing 2 or 3 carbon atoms, which carbon atoms may be substituted by a methyl or ethyl radical;

n represents a whole number between zero and 4; as well as the tris-(ether-amines) thus obtained.

U.S. Pat. No. 2,285,419 discloses the preparation of alkoxy amines of formula (A):

$$_{3-m}H\text{-}N\text{-}[(CH_2\text{-}CH_2O)_1 \text{ or } _2 R]_m \qquad (A)$$

in which R represents a lower alkyl radical and m represents a whole number equal to 1, 2, or 3, by reaction of ammonia with the corresponding ethylene glycol mono-ether in the presence of a hydrogenation-dehydrogenation catalyst. In accordance with a variant of the process, the ammonia can be replaced by an amine of formula (A) in which m is equal to 1 or 2. This process requires long reaction times and makes it possible to obtain only low yields of the desired alkoxy amines. It can, therefore, not be used industrially. In particular, it is by no means adapted to the industrial preparation of tertiary amines of formula (A) in which m is equal to 3.

It has been proposed in French Pat. No. 1,302,365 to improve the yields of alkoxy amines by carrying out the ammonolysis operation in the vapor phase and by furthermore operating in the presence of hydrogen. While such a process makes it possible to improve the yields of alkoxy amines, it does not provide a solution with respect to the obtaining of tertiary amines in selective fashion.

In Belgian patent No. 849,348, it has been proposed to prepare selectively secondary ether-amines of formula (B):

$$\begin{array}{cc} X & Y \\ | & | \\ HN\text{—}[(CH\text{—}CH\text{—}O\text{—})_n R]_2 \end{array} \qquad (B)$$

in which R represents a $C_9$-$C_{24}$ alkyl, cyclohexyl, or aryl radical, X and Y represent a hydrogen atom or a methyl radical, and n represents a whole number between 1 and 15, by reaction in liquid phase of the corresponding alkylene glycol mono-ether with ammonia and hydrogen in the presence of a hydrogenation-dehydrogenation catalyst at a temperature between 150° and 250° C., under a pressure of 0.5 to 1.5 atmospheres and evacuation of the water of reaction with the gaseous stream. Said Belgian patent No. 849,348 describes a process which makes it possible to obtain secondary ether-amines with good selectivity, but it in no way indicates how to proceed in order to direct the ammonolysis reaction in the direction of the formation of tertiary amines.

It is, accordingly, an object of the present invention to provide a process for producing tris-(ether-amines) which is not subject to the difficulties of the processes of the prior art.

It is also an object of the present invention to provide novel tris-(ether-amines).

It is a further object of the invention to provide a useful and effective process for the production of tris-(ether-amines) which is particularly suitable for industrial application.

Other objects of the invention will be apparent to those skilled in the art from the present description.

GENERAL DESCRIPTION OF THE INVENTION

By the present invention it has been found possible to provide a process for selectively preparing tris-(ether-amines) of formula (I) by ammonolysis of the corresponding alkylene glycol mono-ethers.

The process of preparing said tris-(ether-amines) of formula (I):

$$N\text{-}[A\text{-}O\text{-}(B\text{-}O)_n\text{-}R]_3 \qquad (I)$$

in which R represents a member selected from the class consisting of an alkyl radical containing from about 1 to 24 carbon atoms, preferably from about 1 to 12, a cyclohexyl radical, a phenyl radical, and an alkylphenyl radical whose alkyl group contains from about 1 to 12 carbon atoms;

A and B are similar or different and represent a linear alkanediyl group containing 2 or 3 carbon atoms, which carbon atoms may be substituted by a methyl or ethyl radical, and n represents a whole number between zero and 4, preferably between zero and 3; by ammonolysis in the liquid phase of an alkylene glycol mono-ether of formula (II):

$$HO\text{-}A\text{-}O\text{-}(B\text{-}O)_n\text{-}R \qquad (II)$$

in which R, A, B and n have the meanings given above, by means of at least one ammonolysis agent selected from among the class of ammonia and an ether-amine of formula (III):

$$(3-p HN)\text{-}[A'\text{-}O\text{-}(B'\text{-}O)_{n'}\text{-}R']_p \qquad (III)$$

in which R', A', B', and n' are identical to R, A, B, and n, respectively, and p is equal to 1 or 2, in the presence of a hydrogenation-dehydrogenation catalyst, at a temperature between about 150° and 250° C., preferably between about 175° and 220° C., in which the said ammonolysis operation is carried out by contacting the ammonolysis agent or agents with a mixture containing the said alkylene glycol mono-ether of formula (II) and the said hydrogenation-dehydrogenation catalyst, with the amount of the said catalyst being between about 10 and 40 percent by weight, based on the weight of said alkylene glycol mono-ether. Thereafter, the desired tris-(ether-amine) formed is removed from the reaction mixture.

The presence of hydrogenation-dehydrogenation catalyst in the said sufficient amount of between about 10 and 40 percent is fundamental for the reaction to take place in the direction of the formation of tertiary tris-(ether-amines). The amount of said catalyst is preferably between about 10 and 35 percent of the weight of alkylene glycol mono-ether.

The conventional hydrogenation-dehydrogenation catalysts may be used, including Raney cobalt and Raney copper, but nickel catalysts of the Raney or Harshaw nickel type are, however, preferred.

For the satisfactory conduct of the process of the invention, the ammonolysis operation is preferably carried out in the presence of hydrogen at a pressure of less than 20 bars, and generally at autogenous pressure, with vigorous agitation until disappearance of the alkylene glycol mono-ether. This operation normally takes from about 2 to 10 hours and generally about 3 to 8 hours.

Among the alkylene glycol mono-ethers which can be employed as starting materials are:
-3-oxa-1-butanol
-3,6-dioxa-1-heptanol
-3,6,9-trioxa-1-decanol
-3-oxa-1-pentanol
-3,6-dioxa-1-octanol
-3,6,9-trioxa-1-undecanol
-3-oxa-1-hexanol
-3,6-dioxa-1-nonanol
-3,6,9-trioxa-1-dodecanol
-3-oxa-1-heptanol
-3,6-dioxa-1-decanol
-3,6,9-trioxa-1-tridecanol
-5-phenoxy-3-oxa-1-pentanol
-8-phenoxy-3,6-dioxa-1-octanol
-5-cyclohexoxy-3-oxa-1-pentanol
-8-cyclohexoxy-3,6-dioxa-1-octanol
-5-nonylphenoxy-3-oxa-1-pentanol
-8-nonylphenoxy-3,6-dioxa-1-octanol
-5-dodecylphenoxy-3-oxa-1-pentanol
-8-dodecylphenoxy-3,6-dioxa-1-octanol
-3,6-dioxa-4-methyl-1-heptanol, and
-3,6-dioxa-2,4-dimethyl-1-heptanol.

Among the secondary or primary ether-amines of formula (III), above, which may be employed are:

As Secondary Amines
-5-aza-2,8-dioxa-nonane
-8-aza-2,5,11,14-tetraoxa-pentadecane
-11-aza-2,5,8,14,17,20-hexoxa-uneicosane
-6-aza-3,9-dioxa-undecane
-10-aza-4,7,13,16-tetraoxa-nonadecane
-9-aza-3,6,12,15-tetraoxa-heptadecane
-12-aza-3,6,9,15,18,21-hexaoxa-tricosane
-7-aza-4,10-dioxa-tridecane
-13-aza-4,7,10,16,19,22-hexaoxa-pentacosane
-8-aza-5,11-dioxa-pentadecane
-11-aza-5,8,14,17-tetraoxa-uneicosane
-14-aza-5,8,11,17,20,23-hexaoxa-heptacosane
-6-aza-3-oxa-1-phenoxy-undecane
-9-aza-3,6-dioxa-1-phenoxy-heptadecane
-6-aza-3-oxa-1-cyclohexoxy-undecane
-9-aza-3,6-dioxa-1-cyclohexoxy-heptadecane
-6-aza-3-oxa-1-nonylphenoxy-undecane
-9-aza-3,6-dioxa-1-nonylphenoxy-heptadecane
-6-aza-3-oxa-1-dodecylphenoxy-undecane
-9-aza-3,6-dioxa-dodecylphenoxy-heptadecane
-8-aza-2,5,11,14-tetraoxa-4,12-dimethyl-pentadecane, and
-8-aza-2,5,11,14-tetraoxa-4,6,10,12-tetramethyl-pentadecane.

As Primary Amines
-3-oxa-butylamine
-3-oxa-pentylamine
-3-oxa-hexylamine
-3-oxa-heptylamine
-3,6-dioxa-eptylamine
-3,6,9-trioxa-undecylamine
-3,6-dioxa-octylamine
-3,6,9-trioxa-dodecylamine
-3,6-dioxa-nonylamine
-3,6,9-trioxa-tridecylamine
-3,6-dioxa-decylamine
-3,6,9-trioxa-tetradecylamine
-5-phenoxy-3-oxa-pentylamine
-8-phenoxy-3,6-dioxa-octylamine
-5-cyclohexoxy-3-oxa-pentylamine
-8-cyclohexoxy-3,6-dioxa-octylamine
-5-nonylphenoxy-3-oxa-pentylamine
-8-nonylphenoxy-3,6-dioxa-octylamine
-5-dodecylphenoxy-3-oxa-pentylamine
-8-dodecylphenoxy-3,6-dioxa-octylamine
-3,6-dioxa-4-methyl-heptylamine, and
-3,6-dioxa-1,2,4-dimethyl-heptylamine.

When the ammonolysis agent used is ammonia, it can be employed in varying quantities which are not critical. However, it is desirable to operate in the presence of a large surplus of ammonia over the amount stoichiometrically required for the obtaining of tertiary ether-amines, for instance, in the presence of at least twice this stoichiometric amount, and, preferably, between about 2 and 5 times this stoichiometric amount.

The amount of hydrogen which is employed is also not critical. It is advisable to employ from about 1 to 50 percent by weight of hydrogen, based on the weight of ammonia, preferably from about 2 to 30 percent of the weight of ammonia employed.

In accordance with a variant of the process, the ammonolysis operation is conducted in a stream of ammonia and hydrogen until about 50 to 66 percent, approximately, of the alkylene glycol mono-ether has been transformed into amines, whereupon the operation is permitted to come to completion in the stream of hydrogen alone.

When the ammonolysis agent employed is a secondary or primary ether-amine corresponding to the desired tris-(ether-amine), it will generally be favorable to operate with a molar ratio of alkylene glycol mono-ether to secondary or primary ether-amine of at least about 1.3 times the ratio stoichiometrically required for the obtaining of a tris-(ether-amine). This ratio can generally be from about 1.4 to 4 times the stoichiometric amount.

The amount of hydrogen which is employed is desirably from about 1 to 10 percent of the weight of alkylene glycol mono-ether used, preferably from about 1 to 5 percent.

The water of reaction formed during the course of the ammonolysis reaction must be eliminated from the reaction medium, desirably by means of sweeping it with a stream of gas. When ammonia and/or hydrogen are used, the water is entrained by said gas or gases. When operating under autogenous pressure, a slight leakage of gas will make it possible both to regulate the pressure and to eliminate the water formed. When no gas is used, the water of reaction can be entrained, for instance, by nitrogen.

The ammonolysis operation is followed by a step for the removal of the tris-(ether-amine) formed. This step may be carried out by any known means, for instance, by distillation.

The process of the invention is preferably carried out batchwise. However, it may be carried out continuously, since the products which have not been completely transformed into tertiary amines correspond to the secondary and/or primary ether-amines which can be used as the ammonolysis agent. Furthermore, the catalyst retains its activity and can be recycled.

The process forming the object of the invention is particularly well adapted to the selective preparation of tris-(ether-amines), such as:
- tris-(3-oxabutyl)amine
- tris-(3,6-dioxaheptyl)amine
- tris-(3,6,9-trioxadecyl)amine
- tris-(3-oxapentyl)amine
- tris-(3,6-dioxaoctyl)amine
- tris-(3,6,9-trioxaundecyl)amine
- tris-(3-oxahexyl)amine
- tris-(3,6-dioxanonyl)amine
- tris-(3,6,9-trioxadodecyl)amine
- tris-(3-oxaheptyl)amine
- tris-(3,6-dioxadecyl)amine
- tris-(3,6,9-trioxatridecyl)amine
- tris-(3,6-dioxa-4-methylheptyl)amine
- tris-(3,6-dioxa-2,4-dimethylheptyl)amine
- tris-(5-phenoxy-3-oxapentyl)amine
- tris-(8-phenoxy-3,6-dioxaoctyl)amine
- tris-(5-cyclohexoxy-3-oxapentyl)amine
- tris-(8-cyclohexoxy-3,6-dioxaoctyl)amine
- tris-(5-nonylphenoxy-3-oxapentyl)amine
- tris-(8-nonylphenoxy-3,6-dioxaoctyl)amine
- tris-(5-dodecylphenoxy-3-oxapentyl)amine, and
- tris-(8-dodecylphenoxy-3,6-dioxaoctyl)amine.

The present invention is also directed to the tris-(polyoxaalkyl)amines obtained by the process of the invention.

These tertiary amines of the invention can be used as sequestrating agents in order to solubilize inorganic and/or organometallic salts in organic solvents in which they are not soluble, or in order to increase the solubility of organic or organometallic salts in organic solvents as disclosed in copending U.S. application of Grerard Soula, filed Feb. 29, 1980, commonly assigned, entitled "Process For Solubilizing Organic or Mineral Salts in Organic Solvents". These tertiary amines can also be used as emulsifiers.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

Preparation of tris-(3,6-dioxaoctyl)amine of the formula:

N(CH$_2$-CH$_2$-O-CH$_2$-CH$_2$-O-C$_2$H$_5$)$_3$

Into a four-neck flask provided with an agitator, ammonia and hydrogen inlet, a column, and a condenser for collecting the water entrained by the gaseous stream, there were introduced 195 g. of dehydrated Raney nickel and 1400 g. of 3,6-dioxa-octanol (ethyl mono-ether of diethylene glycol).

The slurry obtained was brought to a temperature of 150° C., at which temperature a gaseous stream consisting of 51 g. of ammonia and 2 g. of hydrogen per hour was passed through. The slurry was then heated to 185° C., at which temperature it was held for 3 hours. About 60 percent of the alkylene glycol ether had been converted into amines. The feeding of the ammonia was then stopped, while maintaining the stream of hydrogen for an additional 2 hours at 185° C. After cooling, the Raney nickel was filtered off, whereupon the filtrate was distilled under vacuum.

There were obtained:

800 g. of tris-(3,6-dioxaoctyl)amine having a boiling point of 195° C. under 0.5 mm. Hg., and 180 g. of 9-aza-3,6,12,15-tetraoxa-heptadecane having a boiling point of 143° C. at a pressure of 0.5 mm. of mercury.

The conversion rate of the 3,6-dioxaoctanol was 95 percent. The yields were:

63 percent tris-(3,6-dioxa)octyl-amine, 14 percent 9-aza-3,6,12,15-tetraoxa-heptadecane, the balance being diethoxy ethane.

The ammonolysis operation described above was carried out while varying the different amounts of Raney nickel used.

The results obtained after a given period of reaction were as follows:

| % by weight of Ni referred to the ether alcohol | 3 | 6 | 8.6 | 13.9 | 16 |
|---|---|---|---|---|---|
| rate of conversion of the ether alcohol (%) | 98 | 94 | 96 | 95 | 96 |
| yield of tertiary amine (%) | .2 | 5 | 23 | 63 | 61 |
| yield of secondary amine (%) | 75 | 68 | 54 | 14 | 16 |

This table shows the importance which the amount of catalyst used has on the course of the reaction, particularly on the yield of desired tertiary amine.

EXAMPLE 2

Preparation of tris-(3,6,9-trioxa-undecyl)amine of the formula:

N(CH$_2$-CH$_2$-O-CH$_2$-CH$_2$-O-CH$_2$-CH$_2$-OC$_2$H$_5$)$_3$

Into a four-neck flask there were introduced 133 g. of 12-aza-3,6,9,15,18,21-hexaoxa-tricosane of the formula NH(CH$_2$-CH$_2$-O-CH$_2$-CH$_2$-O-CH$_2$-CH$_2$-OC$_2$H$_5$)$_2$, 20 g. of Raney nickel, and 180 g. of 3,6,9-trioxa-undecanol.

The mixture was heated for 6 hours at 195° C. under a stream of hydrogen of about 2 g. per hour.

After filtration of the Raney nickel, the tris-(ether-amine) was distilled.

There were thus obtained 156 g. of tris-(3,6,9-trioxa-undecyl)amine, namely, a yield of 66 percent based on the amount of alkylene glycol ether.

EXAMPLE 3

Preparation of tris-(3,6-dioxa-heptyl)amine of the formula:

N(CH$_2$-CH$_2$-O-CH$_2$-CH$_2$O-CH$_3$)$_3$

The operation described in Example 1 was carried out starting with 7500 g. of Raney nickel, 25,000 g. of 3,6-dioxa-1-heptanol, 1700 g. per hour of ammonia, and 50 g. per hour of hydrogen.

The conversion rate of the ether alcohol was 90 percent.

The yields were:

50 percent of tris-(3,6-dioxa-heptyl)amine of boiling point of 160° C. at 0.5 mm. Hg.;

20 percent of 8-aza-2,5,11,14-tetraoxa-pentadecane of boiling point of 125° C. at 0.5 mm. Hg.

EXAMPLE 4

Preparation of tris-(3,6-dioxa-decyl)amine of the formula:

N(CH$_2$-CH$_2$-O-CH$_2$-CH$_2$-O-C$_4$H$_9$)$_3$

The operation described in Example 1 was carried out starting with 150 g. of Raney nickel, 558 g. of 3,6-dioxa-1-decanol, 34 g. per hour of ammonia, and 4 g. per hour of hydrogen.

The conversion rate of the ether alcohol was 90 percent.

The yields were:

50 percent tris-(3,6-dioxa-decyl)amine of boiling point of 240° C. at 0.5 mm. Hg.;

22 percent 11-aza-5,8,14,17-tetraoxa-heneicosane of boiling point of 160° C. at 0.6 mm. Hg.

EXAMPLE 5

Preparation of tris-(3,6-dioxa-octyl)amine

Into the apparatus described in Example 1 there were introduced 300 g. of Harshaw nickel and 1270 g. of 3,6-dioxa-1-octanol. The resulting slurry was brought to 150° C. and a stream of gas passed therethrough consisting of 68 g. per hour of ammonia and 3 g. per hour of hydrogen.

Heating was effected to a temperature of 185° C., and this temperature was maintained for 6 hours and 30 minutes. The stream of ammonia was maintained during the entire operation.

After cooling, filtration, and distillation, the conversion rate of the ether alcohol was 96 percent.

The yields were:

60 percent of tris-(3,6-dioxa-octyl)amine, and 15 percent of 9-aza-3,6,12,15-tetraoxa-heptadecane.

EXAMPLE 6

Into the apparatus described in Example 1 there were introduced 150 g. of Raney nickel, 800 g. of 9-aza-3,6,12,15-tetraoxa-heptadecane, and 700 g. of 3,6-dioxa-octanol.

Heating was effected for 4 hours at 185° C., under a stream of 2 g. per hour of hydrogen.

After cooling, filtration, and distillation, the conversion rate of the ether alcohol was 75 percent. The yield of tris-(3,6-dioxa-octyl)amine was 86 percent.

EXAMPLE 7

The operation described in Example 1 was carried out starting with 250 g. of Raney nickel, 1250 g. of 3,6-dioxa-octanol, 51 g. per hour of ammonia, and 2 g. per hour of hydrogen.

After cooling, the nickel was allowed to settle out and there were withdrawn 950 g. of liquid consisting of 60.5 percent tris-(3,6-dioxa-heptyl)amine and 14.5 percent of secondary amine.

25 g. of new Raney nickel were charged onto the deposit of nickel remaining in the apparatus, as well as 1250 g. of 3,6-dioxa-octanol. The ammonolysis operation was repeated under the same conditions. After cooling and decantation, 1100 g. of liquid containing 60.1 percent of tris-(3,6-dioxa-heptyl)amine and 14.7 percent of secondary amine were withdrawn.

This operation was carried out a total of 5 successive times. At the end of the fifth time, the yield of tris-(3,6-dioxa-heptyl)amine was still 59.2 percent.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. An improved process of preparing tris-(ether-amines) of formula (I):

(I) N-[A-O-(B-O)$_n$R]$_3$     (I)

in which R represents a member selected from the class consisting of an alkyl radical containing from about 1 to 24 carbon atoms, a clcylohexyl radical, a phenyl radical, and an alkylphenyl radical whose alkyl group contains from about 1 to 12 carbon atoms;

A and B are similar or different and represent a linear alkanediyl group containing 2 or 3 carbon atoms, and n represents a whole number between zero and 4, by ammonolysis in liquid phase of an alkylene glycol mono-ether of formula (II):

HO-A-O-(B-O-)$_n$R     (II)

in which R, A, B, and n ave the meaning given above, by means of at least one ammonolysis agent selected from among ammonia and the ether-amines of formula (III):

(3-$_p$HN)-[A'-O-(B'-O-)$_n$'R']$_p$     (III)

in which R', A', B', and n' are identical to R, A, B, and n, respectively, and p is equal to 1 or 2, in the presence of a hydrogenation-dehydrogenation catalyst at a temperature of between about 150° and 250° C. followed by recovery of the tris-(ether-amine) formed, the improvement consisting of using an amount of said catalyst between about 10 and 40 percent by weight based on the weight of the alkylene glycol mono-ether employed.

2. A process according to claim 1, wherein the at least one carbon atom of the alkanediyl groups comprising A and B are substituted by a group selected from the class of methyl and ethyl radicals.

3. A process according to claim 1, wherein n represents a whole number between zero and 3, and R contains from about 1 to 12 carbon atoms when it represents an alkyl radical.

4. A process according to claim 1, wherein the ammonolysis operation is carried out at a temperature of between about 175° and 220° C.

5. A process according to claim 1, wherein the ammonolysis operation is carried out in the presence of from about 10 to 35 percent by weight of hydrogenation-dehydrogenation catalyst, based on the weight of alkylene glycol mono-ether.

6. A process according to claim 1, wherein the hydrogenation-dehydrogenation catalyst employed is a nickel catalyst.

7. A process according to claim 1, wherein the alkylene glycol mono-ether of formula (II) is selected from among:
- -3-oxa-1-butanol
- -3,6-dioxa-1-heptanol
- -3,6,9-trioxa-1-decanol
- -3-oxa-1-pentanol
- -3,6-dioxa-1-octanol
- -3,6,9-trioxa-1-undecanol
- -3-oxa-1-hexanol
- -3,6-dioxa-1-nonanol
- -3,6,9-trioxa-1-dodecanol
- -3-oxa-1-heptanol
- -3,6-dioxa-1-decanol
- -3,6,9-trioxa-1-tridecanol
- -5-phenoxy-3-oxa-1-pentanol
- -8-phenoxy-3,6-dioxa-1-octanol
- -5-cyclohexoxy-3-oxa-1-pentanol
- -8-cyclohexoxy-3,6-dioxa-1-octanol
- -5-nonylphenoxy-3-oxa-1-pentanol
- -8-nonylphenoxy-3,6-dioxa-1-octanol
- -5-dodecylphenoxy-3-oxa-1-pentanol
- -8-dodecylphenoxy-3,6-dioxa-1-octanol
- -3,6-dioxa-4-methyl-1-heptanol, and
- -3,6-dioxa-2,4-dimethyl-1-heptanol.

8. A process according to claim 1, wherein the ammonolysis is carried out in the presence of hydrogen.

9. A process according to claim 1, wherein the ammonolysis agent is ammonia and it is used in amounts corresponding to at least about twice the stoichiometric quantity.

10. A process according to claim 9, wherein the amount of ammonia used is between about 2 and 5 times the stoichiometric amount.

11. A process according to claim 9 or claim 10, wherein the ammonolysis is carried out in the presence of from about 1 to 50 percent by weight of hydrogen, based on weight of the ammonia.

12. A process according to claim 11, wherein the amount of hydrogen is between about 2 and 30 percent of the weight of ammonia.

13. A process according to either of claims 11 and 12, wherein the ammonolysis is carried out in a stream of ammonia and hydrogen until about 50 to 60 percent of the alkylene glycol mono-ether is converted, whereupon it is terminated in a stream of hydrogen.

14. A process according to claim 1, wherein the ammonolysis agent is a primary or secondary ether-amine, the amount of primary or secondary ether-amine employed is such that the ratio of alkylene glycol mono-ether to primary or secondary ether-amine is equal to at least about 1.3 times the stoichiometric ratio.

15. A process according to claim 14, wherein the ratio of alkylene glycol mono-ether to primary or secondary ether-amine is between about 1.4 and 4 times the stoichiometric ratio.

16. A process according to either of claims 14 or 15, wherein the ammonolysis is carried out by means of a primary or secondary ether-amine and is effected in the presence of from about 1 to 10 percent by weight of hydrogen, based on the weight of alkylene glycol mono-ether employed.

17. A process according to claim 16, wherein the amount of hydrogen is between about 1 and 5 percent of the weight of alkylene glycol mono-ether.

18. A process according to either of claims 1 or 14, wherein the primary ether-amine is selected from among the class of:
- -3-oxa-butylamine
- -3-oxa-pentylamine
- -3-oxa-hexylamine
- -3-oxa-heptylamine
- -3,6-dioxa-heptylamine
- -3,6,9-trioxa-undecylamine
- -3,6-dioxa-octylamine
- -3,6,9-trioxa-dodecylamine
- -3,6-dioxa-nonylamine
- -3,6,9-trioxa-tridecylamine
- -3,6-dioxa-decylamine
- -3,6,9-trioxa-tetradecylamine
- -5-phenoxy-3-oxa-pentylamine
- -8-phenoxy-3,6-dioxa-octylamine
- -5-cyclohexoxy-3-oxa-pentylamine
- -8-cyclohexoxy-3,6-dioxa-octylamine
- -5-nonylphenoxy-3-oxa-pentylamine
- -8-nonylphenoxy-3,6-dioxa-octylamine
- -5-dodecylphenoxy-3-oxa-pentylamine
- -8-dodecylphenoxy-3,6-dioxa-octylamine
- -3,6-dioxa-4-methyl-heptylamine, and
- -3,6-dioxa-2,4-dimethyl heptylamine.

19. A process according to either of claims 1 or 14, wherein the secondary any ether amine employed is selected from among the class of:
- -5-aza-2,8-dioxa-nonane
- -8-aza-2,5,11,14-tetraoxa-pentadecane
- -11-aza-2,5,8,14,17,20-hexaoxa-uneicosane
- -6-aza-3,9-dioxa-undecane
- -10-aza-4,7,13,16-tetraoxa-nonadecane
- -9-aza-3,6,12,15-tetraoxa-heptadecane
- -12-aza-3,6,9,15,18,21-hexaoxa-tricosane
- -7-aza-4,10-dioxa-tridecane
- -13-aza-4,7,10,16,19,22-hexaoxa-pentacosane
- -8-aza-5,11-dioxa-pentadecane
- -11-aza-5,8,14,17-tetraoxa-uneicosane
- -14-aza-5,8,11,17,20,23-hexaoxa-heptacosane
- -6-aza-3-oxa-1-phenoxy-undecane
- -9-aza-3,6-dioxa-1-phenoxyheptadecane
- -6-aza-3-oxa-1-cyclohexoxy-undecane
- -9-aza-3,6-dioxa-1-cyclohexoxy-heptadecane
- -6-aza-3-oxa-1-nonylphenoxy-undecane
- -9-aza-3,6-dioxa-1-nonylphenoxy-heptadecane
- -6-aza-3-oxa-1-dodecylphenoxy-undecane
- -9-aza-3,6-dioxa-dodecylphenoxy-heptadecane
- -8-aza-2,5,11,14-tetraoxa-4,12-dimethyl-pentadecane, and
- -8-aza-2,5,11,14-tetraoxa-4,6,10,12-trimethyl-pentadecane.

* * * * *

UNITED STATES PATENT AND TRADEMARK OFFICE
CERTIFICATE OF CORRECTION

PATENT NO. : 4,408,075
DATED : October 4, 1983
INVENTOR(S) : Soula et al.

It is certified that error appears in the above—identified patent and that said Letters Patent is hereby corrected as shown below:

In the list of References Cited, "Zeck" should be --Zech--;

at column 2, line 17, delete "P" at the beginning of the line;

at column 5, line 39, "Grerard" should be --Gerard--;

at column 7, line 55, "75" should be --72--;

at column 8, line 20, delete "(I)" at the beginning of the line; line 24, "clcylohexyl" should be --cyclohexyl--; line 37, "ave" should be --have--; and at column 10, line 35, delete "any"; line 59, "trimethyl" should be --tetramethyl--.

Signed and Sealed this

Twenty-second Day of May 1984

[SEAL]

Attest:

GERALD J. MOSSINGHOFF

Attesting Officer     Commissioner of Patents and Trademarks